(12) United States Patent
Ross

(10) Patent No.: US 7,832,956 B2
(45) Date of Patent: Nov. 16, 2010

(54) DENTAL CLEANSER AND STAIN PREVENTION APPARATUS

(76) Inventor: Karen L. Ross, 2436 Kimberly Ave., Camarillo, CA (US) 93010

( * ) Notice: Subject to any disclaimer, the term of this patent is extended or adjusted under 35 U.S.C. 154(b) by 212 days.

(21) Appl. No.: 11/938,167

(22) Filed: Nov. 9, 2007

(65) Prior Publication Data

US 2009/0123217 A1     May 14, 2009

(51) Int. Cl.
     *A46B 17/04*      (2006.01)
(52) U.S. Cl. .............. 401/269; 401/133; 401/134; 401/183
(58) Field of Classification Search ......... 401/183–186, 401/132–135, 268, 270, 269
See application file for complete search history.

(56) References Cited

U.S. PATENT DOCUMENTS

| | | | |
|---|---|---|---|
| 1,947,720 A * | 2/1934 | Laub ..................... | 401/7 |
| 2,673,362 A | 3/1954 | Robinson | |
| 3,075,639 A | 1/1963 | Lingley | |
| 4,530,129 A | 7/1985 | Labick et al. | |
| 4,880,111 A | 11/1989 | Bagwell et al. | |
| 5,001,803 A | 3/1991 | Discko, Jr. | |
| 5,028,158 A | 7/1991 | Fey | |
| 5,046,212 A | 9/1991 | O'Conke | |
| 5,184,719 A | 2/1993 | Gordon | |
| 5,244,096 A | 9/1993 | Stoner | |
| 5,599,126 A * | 2/1997 | Hough ................... | 401/184 |
| 5,775,511 A | 7/1998 | Stark | |
| 5,954,996 A | 9/1999 | Discko, Jr. | |
| 6,009,886 A | 1/2000 | Labranche et al. | |
| 6,062,233 A | 5/2000 | Williams | |
| 6,311,837 B1 | 11/2001 | Blaustein et al. | |
| 6,401,727 B1 | 6/2002 | Carroll | |
| 6,463,937 B1 | 10/2002 | Cloutier et al. | |
| 6,682,722 B2 | 1/2004 | Majeti et al. | |
| 6,702,113 B2 | 3/2004 | Marino | |
| 6,722,805 B1 * | 4/2004 | Skinner .................. | 401/132 |
| 7,270,239 B1 | 9/2007 | Ross | |
| 7,331,731 B2 | 2/2008 | Hohlbein et al. | |
| 7,416,357 B2 * | 8/2008 | Thiebaut ................ | 401/131 |
| 7,572,079 B2 * | 8/2009 | Wong ..................... | 401/134 |
| 2002/0088474 A1 | 7/2002 | Montalvo | |
| 2003/0203338 A1 | 10/2003 | Levine | |
| 2006/0228158 A1 | 10/2006 | Levine et al. | |
| 2007/0209954 A1 | 9/2007 | Aldridge et al. | |

* cited by examiner

*Primary Examiner*—David J Walczak
(74) *Attorney, Agent, or Firm*—Marvin H. Kleinberg; Marshall A. Lerner; Kleinberg & Lerner, LLP

(57) ABSTRACT

A dental apparatus for cleansing and stain preventing on-the-go is provided in multiple embodiments. One embodiment allows a user to dispose the apparatus after use. Another embodiment allows a user to seal and refill the dental apparatus for repeated use. Further, packaging of various types allows a user to house the dental apparatus in multiple ways.

11 Claims, 19 Drawing Sheets

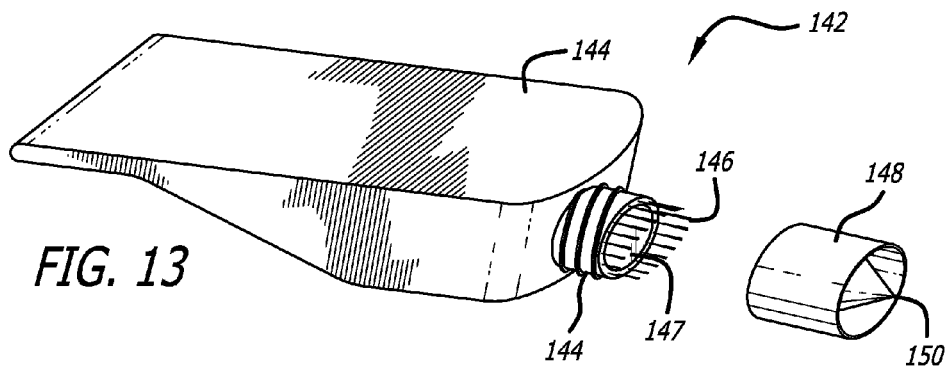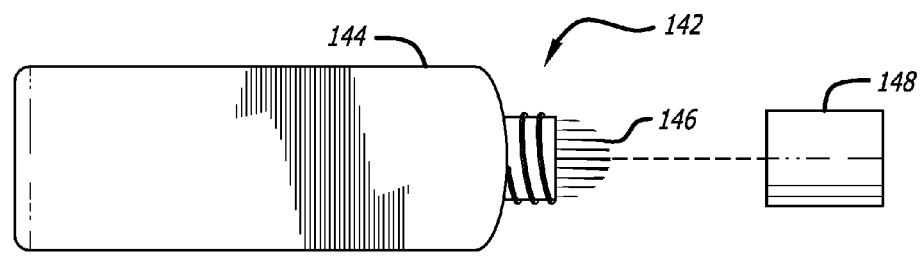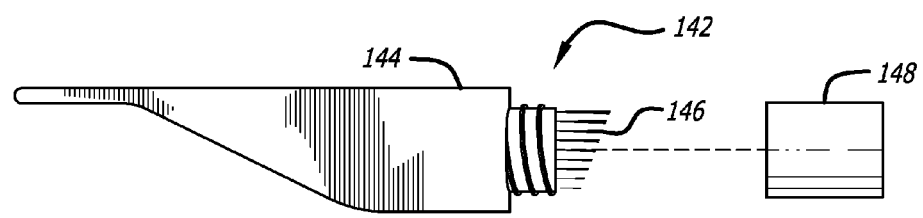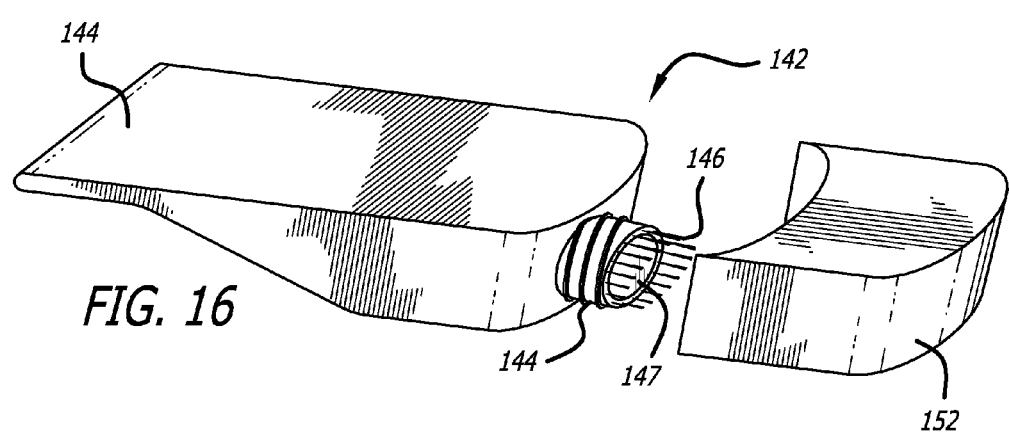

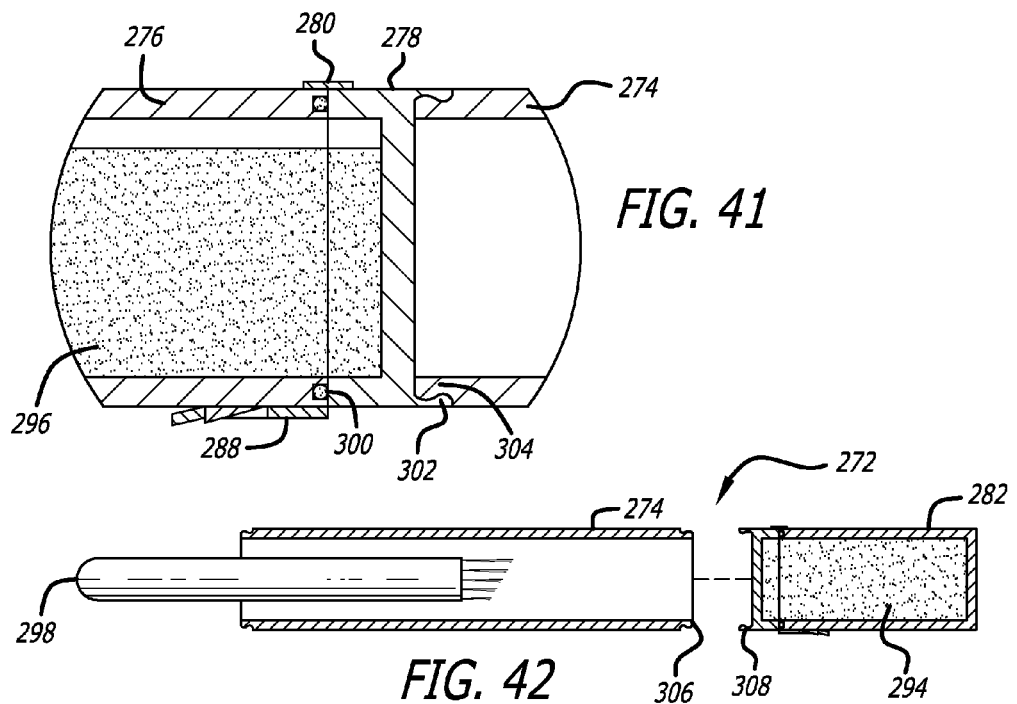
FIG. 41
FIG. 42
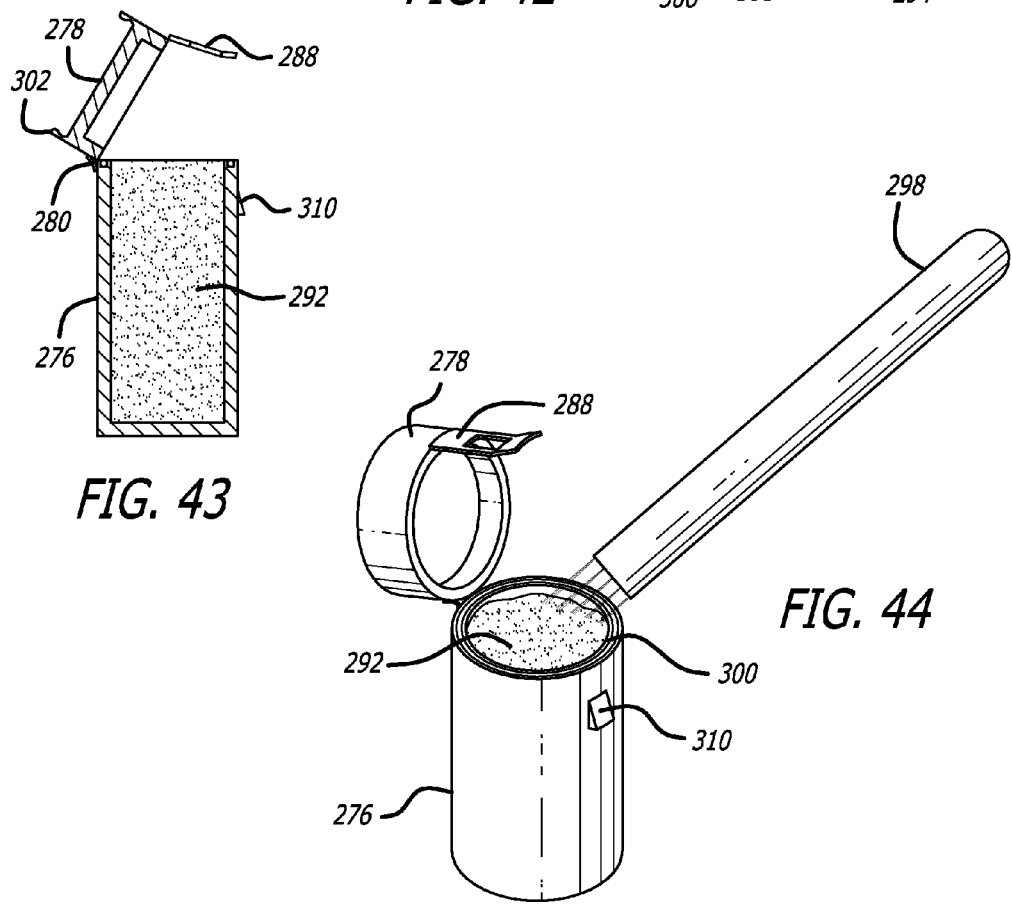
FIG. 43
FIG. 44

DENTAL CLEANSER AND STAIN PREVENTION APPARATUS

BACKGROUND OF THE INVENTION

1. Field of the Invention

The present invention relates to dental cleansing and stain prevention. Specifically, the present invention is a dental cleanser and stain prevention apparatus. The apparatus includes a convenient ready-to-use form of dentifrice or other similar cleansing compound. The apparatus also serves to prevent dental stains through easy transport and access to cleanser while traveling.

2. Description of the Related Art

There exist various other means by which individuals may clean their teeth. In the prior art, there are other apparatus designed for the purpose of cleansing or whitening individual's teeth. The oldest type of dental cleansing apparatus are brushes. Over time, brushes came to be used primarily in conjunction with dentifrice.

The vast majority of dental cleansing apparatus are designed for consistent home use. For example, brushes are often large enough to fit conveniently within a fully clenched hand and have bristles exposed to the open air. Similarly, conscientious purchasers of dentifrice utilize containers that are several inches in length and more than one or two inches in diameter. These large brushes and dentifrice containers serve to allow a user numerous uses before the brush is degraded to a substantial degree and before an individual need purchase additional dentifrice.

Various other means have also been created, including dental whitening fluids and application means. Individuals have long used toothpicks to remove stubborn food in an effort to quickly clean the teeth and remove stubborn unsightly remaining food parties after a meal. Various types of "mouthwash" have also been created to clean the mouth or freshen breath.

Portable dental freshening and cleansing means are desired by the public and are becoming more common. Small articles capable of cleaning or freshening the individual's breath are increasingly popular. For example, "portable" mouthwash concentrated strips have become popular among those who are concerned about dental freshness. Similarly, chewing breath-freshening gum has been popular for several years.

Gum products have also tried to capitalize on the desire to actually clean teeth on the go. Most modern chewing gum manufacturers market at least one significant line of chewing gum as "whitening" or "dental cleansing" gums. Recent television commercials include claims that chewing gum after meals reduces cavities. Other products make similar claims. While these claims may be true, cleansing the teeth with products designed specifically to clean the teeth, rather than products primarily designed to freshen breath or provide sugar as a candy are substantially more effective.

Modern society, especially working professionals and other individuals who care about their appearance and dental health, is an increasingly a mobile society. Unfortunately, the typical full-size brush and dentifrice containers are not convenient for a user to take with them when they are on-the-go. Similarly, the dental freshening products and chewing gums most often provide little or no actual cleansing of the visible front portion teeth. Instead, they freshen breath and remove excess particles from only the back, less visible portion of the teeth where the gum or product is actually chewed.

Individuals desire the ability to take dental cleaning products with them for use a single time or a few times in a convenient, small package. Individuals also desire that the products actually clean the teeth and prevent dental stains from occurring.

Some prior art inventions attempt to provide suitable portable dental cleansers. However, these inventions fail in many respects. Most prior art inventions are bulky, complicated to use or are not suited to single, disposable use that are convenient and do not require the need to visit a restroom. Some of the relevant prior art contains glass portions, unsuitable for transport in a purse or glove compartment. Other prior art provides similar functionality, but does not provide for the maintenance of the dentifrice separate from the applicator until such time as the cleanser apparatus is to be used.

For these reasons, there exists in the prior art a need for a compact, ready-to-use dental cleanser and stain prevention apparatus that possibly may not contain harsh chemical whitening ingredients. There is also a need for such apparatus to maintain the dental cleanser conveniently on, and accessible or dispensable from the apparatus separately from the air and debris prior to use and to maintain the dental cleanser free of contact with outside air which may dry or evaporate or possibly contaminate the cleanser.

There is also a need for a compact, ready-to-use dental cleanser and stain prevention apparatus that may be used several times. In the course of multiple uses, there may be a need to provide a means by which the brush may be cleaned on-the-go. There is further a need for the apparatus to maintain the dental cleanser and the brush separate from each other until use. In an alternative embodiment the dental cleanser, a brush cleanser and the brush are separate from each other until use. These and other needs are addressed by the present invention.

SUMMARY OF THE INVENTION

The invention provides a dental cleanser and stain prevention apparatus for use in maintaining the cleanliness and whiteness of teeth while an individual is on-the-go. The invention provides for a single-use disposable dental cleanser. The invention also provides a dental cleansing apparatus suitable for use on-the-go cleaning in addition to a means by which the brush used for the cleaning may itself be cleaned after use.

The present invention includes multiple embodiments. Several embodiments involve single-use brush and dental cleansing material combinations. In these embodiments, a tapered brush is provided along with a small amount of dentifrice or other suitable dental cleaning material. The tapered brush provides for a more complete cleaning process.

The brush affixed to the end of a chamber includes at least enough dental cleanser for a single use. The chamber may be emptied by squeezing the chamber. The chamber is arranged in one of a series of ways so as to be squeezed by a user. In the preferred embodiment, the dental cleanser is disposed behind a seal which is ruptured, allowing the dental cleanser to exit the chamber through or within the bristles of the brush for quick and easy use. These devices may be housed in a single plastic wrapper.

In another embodiment of the invention, the portable dental cleanser and stain prevention apparatus includes a brush, a dentifrice (or other suitable dental cleaner) and a brush cleanser. There are several ways in which these elements may be combined in a single apparatus.

The brush is maintained in one chamber, the dentifrice is maintained in another and the brush cleanser is maintained in yet another. A user may open the apparatus and gain access to each in turn. First a user accesses the brush, then, with the brush, accesses the dentifrice and applies it to the brush. A user may then clean the user's teeth while on-the-go.

Once the teeth have been suitably cleaned, the user may access the brush cleanser and applies the cleanser to the brush head. The brush cleanser may act alone or in combination with a small amount of water and in some embodiments a napkin to suitably clean the brush. The user may then seal both the dentifrice and the brush cleanser compartments. The brush is now clean and prepared for on-the-go use at a later time.

The brush is then returned to its storage compartment. The brush may then be removed at a later time for use, along with the dentifrice. It may be cleaned repeatedly over the course of many uses until the dentifrice or brush cleanser is exhausted. The user may then replenish the dentifrice or brush cleanser. Alternatively, the entire unit may be disposed of and a new one may be used.

The novel features which are characteristic of the invention, both as to structure and method of the operation thereof, together with further objects and advantages thereof, will be understood from the following description, considered in connection with the accompanying drawings, in which the preferred embodiment of the invention is illustrated by way of example. It is to be expressly understood, however, that the drawings are for the purpose of illustration and description only, and they are not intended as a definition of the limits of the invention.

BRIEF DESCRIPTION OF THE DRAWINGS

FIG. 13 shows a perspective view of an alternative embodiment of the invention.

FIG. 14 shows a plan view of the alternative embodiment of FIG. 13.

FIG. 15 shows an elevation view of the alternative embodiment of FIG. 13.

FIG. 16 shows a perspective view of the alternative embodiment of FIG. 13 with an alternative cap.

FIG. 41 shows a cross-sectional close-up of the snapping mechanism of the apparatus of FIG. 37

FIG. 42 shows the removal of the brush and dental cleansing mixture.

FIG. 43 shows the opening of the container for the dental cleaning mixture.

FIG. 44 shows the application of the dental cleaning mixture to the brush.

DETAILED DESCRIPTION OF THE INVENTION

Figure 1:
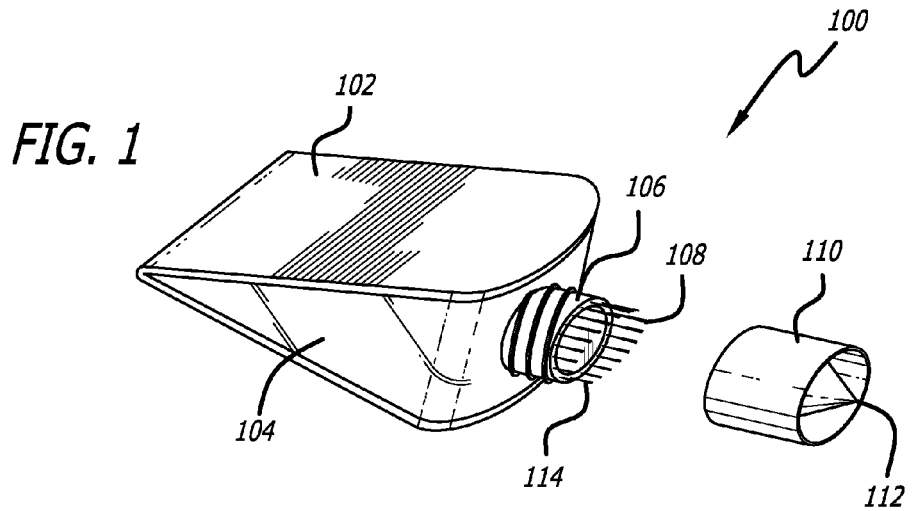
FIG. 1 shows a perspective view of a first embodiment of the dental stain prevention apparatus having a transparent skirt.

Turning first to FIG. 1, a perspective view of one embodiment of the dental cleansing device 100 of the present invention is shown. The dental cleansing device 100 includes an enclosure 102. The enclosure 102 may be of a rigid material or of a pliable material. Similarly, each of the many embodiments shown herein may be made up of rigid or pliable materials. In the preferred embodiment the enclosure is made up of a rigid plastic or rigid metal alloy. In alternative embodiments it may be made up of a very malleable plastic or alloy.

The enclosure 102 in this embodiment generally takes the cross-sectional shape of a "V." A malleable plastic skirt 104 is provided to connect one tip of the "V" with another and to thereby enclose the open area created by the "V" of the enclosure 102. The skirt 104 is clear in this embodiment. As will be seen in later figures, the skirt 104 may instead be translucent or opaque.

Also provided is a threaded neck 106 and a multiplicity of brush-like bristles 108. The threaded neck 106 is used to affix a cap 110 when the device is not in use or has yet to be used. The cap 110 may or may not be equipped with a puncturing point 112 for use in puncturing a seal provided in the base of the threaded neck 106. Furthermore, the cap 110 may or may not be a cap that "snaps on" or "breaks off" for use.

Figure 2:
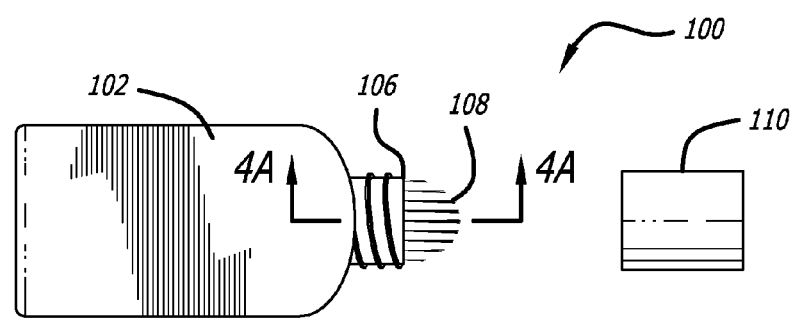
FIG. 2 shows a plan view of a first embodiment of the dental stain prevention apparatus.
Figure 3:
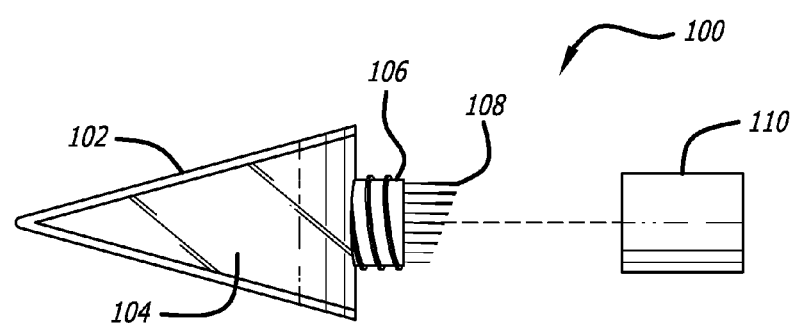
FIG. 3 shows an elevation view of a first embodiment of the dental stain prevention apparatus.

Referring now to FIGS. 2 and 3, a plan perspective and a side perspective of the present embodiment of the invention is shown. Also present in these figure is the enclosure 102, the skirt 104, the threaded neck 106 and the bristles 108. As can be seen, from the top, the bristles 108 appear to be curved in shape (see FIG. 2). From the side, the bristles 108 taper from top to bottom (see FIG. 3). This taper is designed such that the bristles 108 may act more fully and efficiently upon the teeth of a user. Also pictured is the cap 110 for use in protecting the bristles and the contents of the device 100.

Figure 4A:
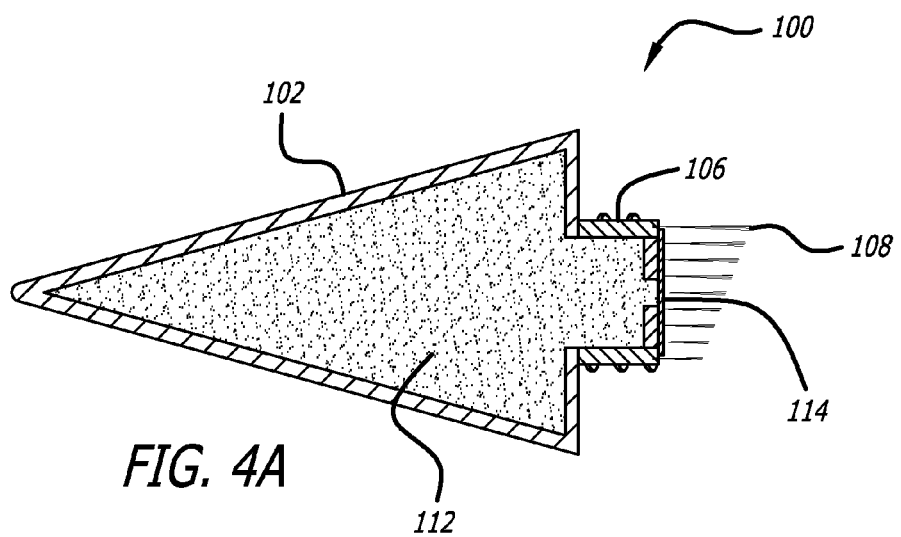
FIGS. 4A and 4B show a cross-section view of a first embodiment of the dental stain prevention apparatus.
Figure 4B:
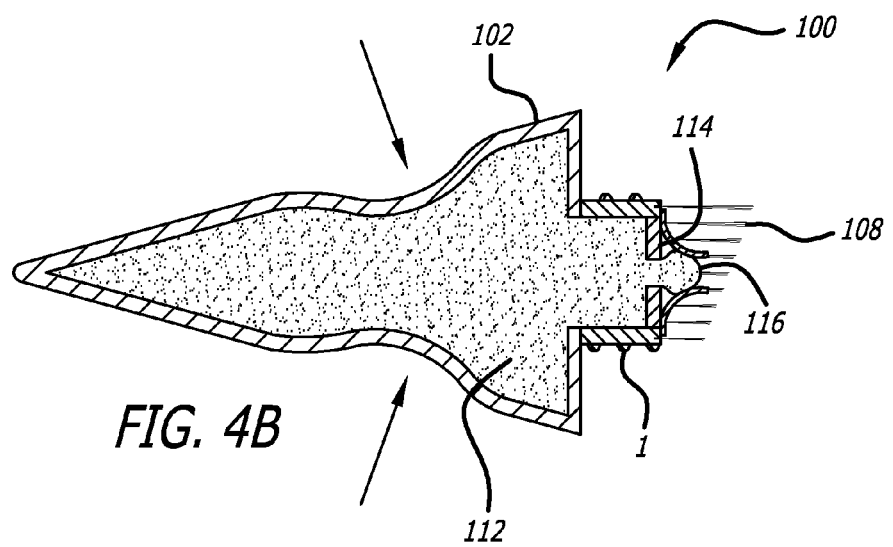

Referring now to FIGS. 4A and 4B, two cross-sectional views of the device 100 of the present invention are shown. In FIG. 4A, the enclosure 102, threaded neck 106 and bristles 108 are shown. In this cross sectional view, the dentifrice 112 may also be seen. Also visible is a seal 114, provided for the protection of the dentifrice 112 when the device has not yet been used.

The term "dentifrice" is applied to the contents of these various dental cleaning apparatus and devices herein. It is to be expressly understood that "dentifrice" refers to any type of dental cleaning fluid or material. In some cases, the "dentifrice" may be contents typically known as "tooth paste." In other cases, "dentifrice" may refer to a dental cleaning fluid or liquid formulated to clean teeth without the use of water or the gritty texture of tooth paste. In other embodiments the "dentifrice" may also be a formulated for specific purposes, such as whitening, sensitive teeth or breath freshening. In other embodiments, it may be a sugar free confectionary type product specifically formulated to freshen breath. An understanding of the term "dentifrice" should be broadening, not narrowing unless specifically indicated.

In FIG. 4A, the seal 114 remains sealed, because the device 100 has not yet been used. It is to be understood that in other embodiments, the seal may be placed at the base of the neck 106 instead of at the head. In FIG. 4B, the seal is shown in the open position.

In some embodiments of the present invention, the seal 114 must first be broken by the puncturing point 112. In other embodiments, the seal 114 may be broken through the application of force to the enclosure 102 as shown in FIG. 4B. This may be provided by creating an intentional weakness in the seal 114 at a point near the middle of the seal 114. This will allow the seal 114 to break in a pre-determined location when pressure is applied to the enclosure 102.

As can be seen in FIG. 4B, the exiting dentifrice 116 moves through a break in the seal 114. This dentifrice 116 is immediately present within the brush bristles 108 and may then be applied to the teeth of a user. The user may then clean his or her teeth.

It may not be clear from a review of FIGS. 1 through 4B that the present invention is intended to be disposable. The device 100 is of a small size, such that a portion of dentifrice 112 is provided that may be used for one to five uses, at which time the device 100 may be thrown away.

Figure 5:
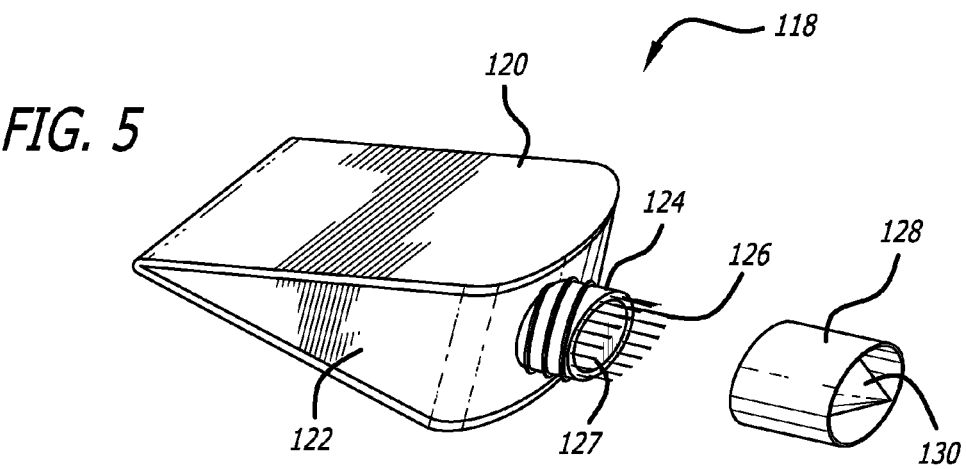
FIG. 5 shows a perspective view of a second embodiment of the dental stain prevention apparatus having an opaque skirt.
Figure 6:
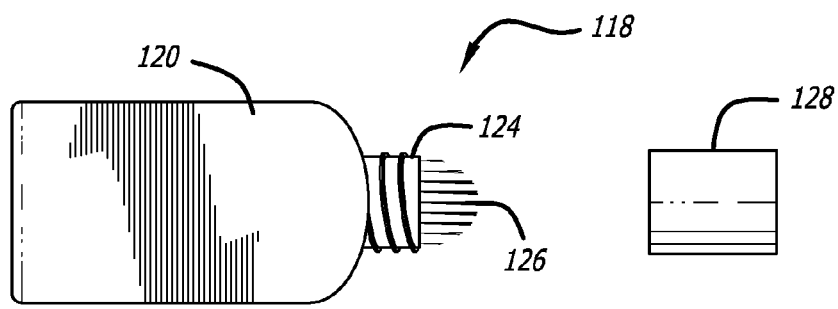
FIG. 6 shows a plan view of a second embodiment of the dental stain prevention apparatus.
Figure 7:
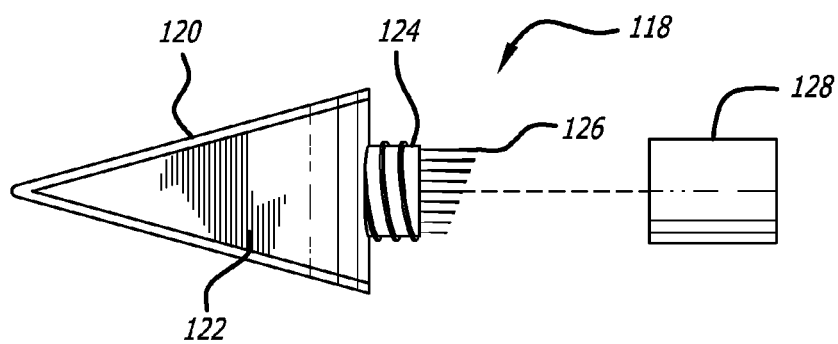
FIG. 7 shows an elevation view of a second embodiment of the dental stain prevention apparatus.

Referring now to FIGS. 5 through 7, an alternative embodiment of the present invention having an opaque skirt 122 is shown. The device 118 includes an enclosure 120. As above, the enclosure 120 may be malleable or may be rigid. The device 118 includes an opaque or translucent skirt 122. The skirt 104 above was transparent. In this embodiment, the primary difference from the prior embodiment is that the skirt 122 is not transparent.

In some instances, transparency may be useful for allowing a user to judge the extent to which the dentifrice product has been depleted. This may be easily ascertained by viewing the interior of the device 100. In other embodiments, such as this one, the transparency may not be necessary and a user may determine the amount present in the device 118 through other means. Opacity or translucency provides for a more uniform appearance of the entire device 118.

Also present in the device 118 shown in FIGS. 5 through 7 are the threaded neck 124, the tapered bristles 126, the cap 128 and the puncturing point 130. As above, the puncturing point 130 may or may not be provided and may or may not be necessary to break a seal 127.

Figure 8:
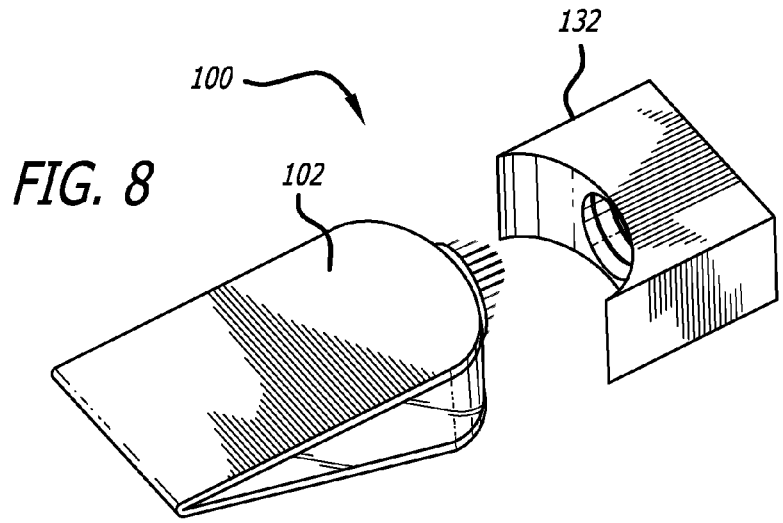
FIG. 8 shows a perspective view of the first embodiment including an alternative cap.
Figure 9:
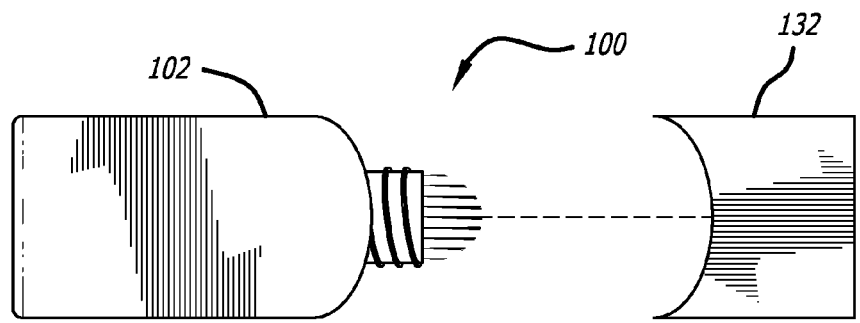
FIG. 9 shows a plan view of one embodiment including the alternative cap of FIG. 9.
Figure 10:
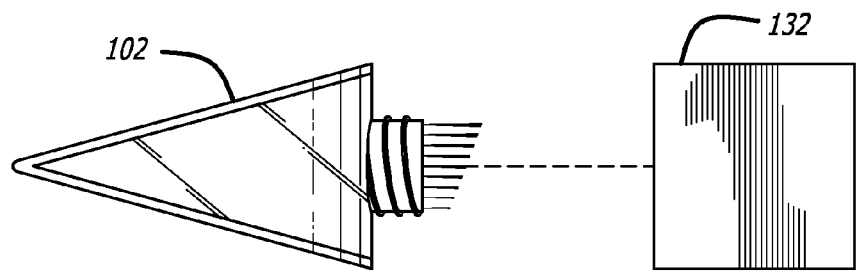
FIG. 10 shows an elevation view of the first embodiment including the alternative cap of FIG. 9.

Referring now to FIGS. 8 through 10, an alternative cap 132 for the device 100 (or alternatively the device 118) is shown. This cap 132 provides a wide, rectangular head matching the top of the enclosure 102. The cap 132 may screw or snap on. It is to be understood that the cap 110 and cap 128 may snap or break on and off as well as utilize threads to stay affixed to the devices 100 and 118, respectively. Similarly, threads may not be provided in the necks 106 and 124, respectively.

The alternative cap 132 provides a means by which the devices 100 and 118 may be stored within containers (shown in FIGS. 33-36). The alternative cap 132 allows the user to more readily grasp the devices 100 and 118 when they are stored within various types of containers. It also provides means by which the devices 100 and 118 may be stored within a purse or other small bag and may be more easily recognized by a user searching for them amongst other items. The cap may also be shaped to aid in packaging or for novel differentiation from other products.

Figure 11:
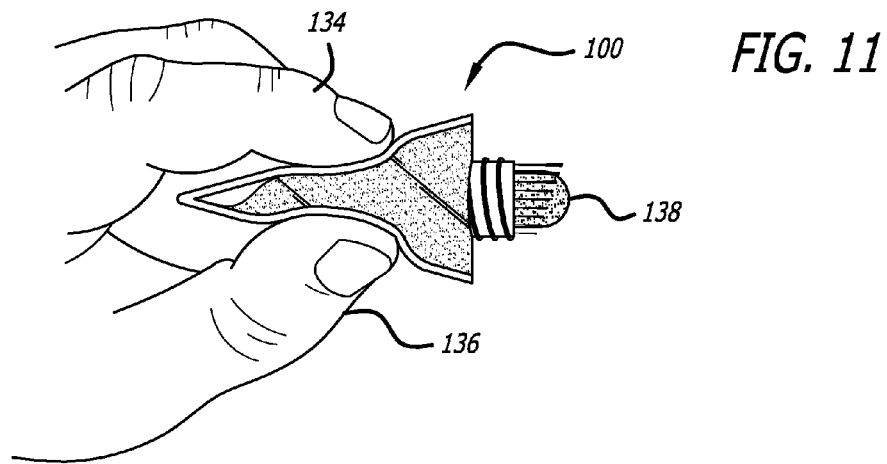
FIG. 11 shows a partial cross-section view of the first embodiment of the dental stain prevention apparatus in use.
Figure 12:
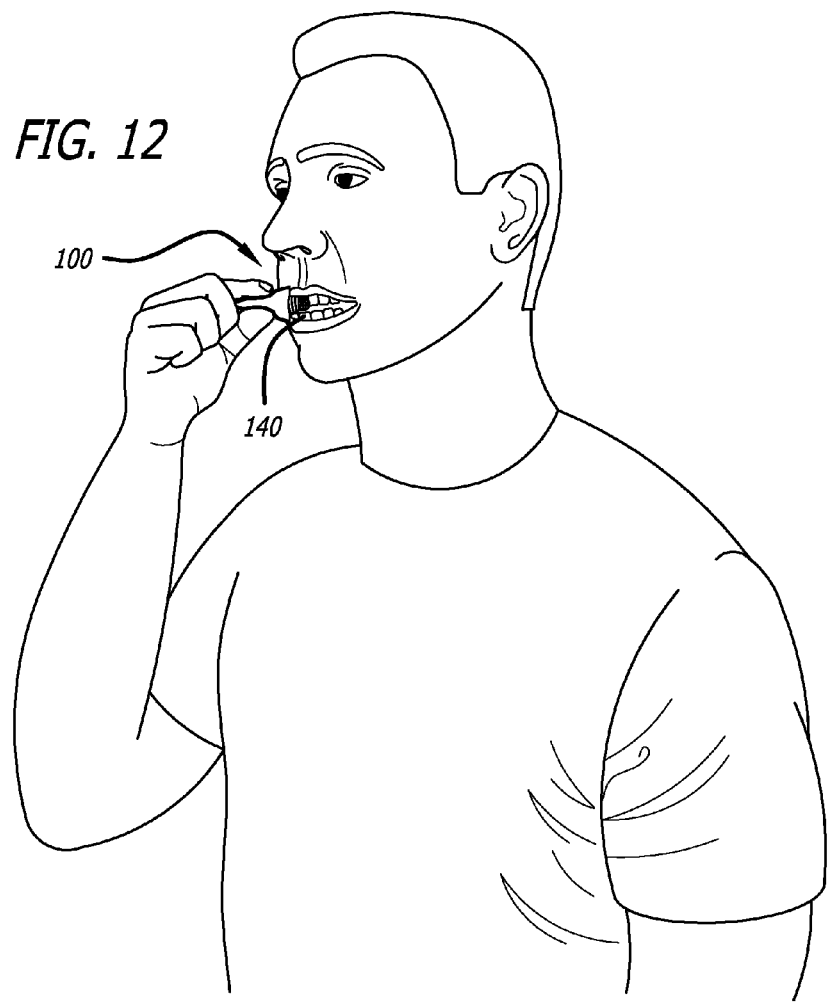
FIG. 12 shows the first embodiment of the dental stain prevention apparatus in use.

Referring now to FIGS. 11 and 12, the device 100 is shown in use. As force is applied to the device 100, for example by means of a forefinger 134 and thumb 136, the dentifrice 138 exits the device 100 near the bristles of the device 100. It is to be understood that this process is also for the device 118 and the embodiments of the present invention shown in FIGS. 13 through 32 as well.

Referring to FIG. 12, the device 100 is then placed near the teeth 140 of the user who may then apply the dentifrice 138 to the teeth 140 and use the bristles to brush and clean the teeth. After one or more uses, the device 100 may then be thrown away.

Another alternative embodiment of the present invention is shown in FIGS. 13 through 16. In this embodiment of the device 142, the enclosure 144 is tapered at one end to allow its use to be more accessible and easy for a user. Similar to previous embodiments, the exterior may be made of malleable plastic or alloys. There are a threaded neck 144, tapered bristles 146, a cap 148 and a puncturing point 150.

The neck 144 includes a seal 147 to maintain the dentifrice 138 in a suitable state for use. It is to be understood that the threaded neck 144 may be replaced with a non-threaded neck of a "snap on," "break off" or similar type. As before, an alternative cap 152 may also be provided.

Figure 17:
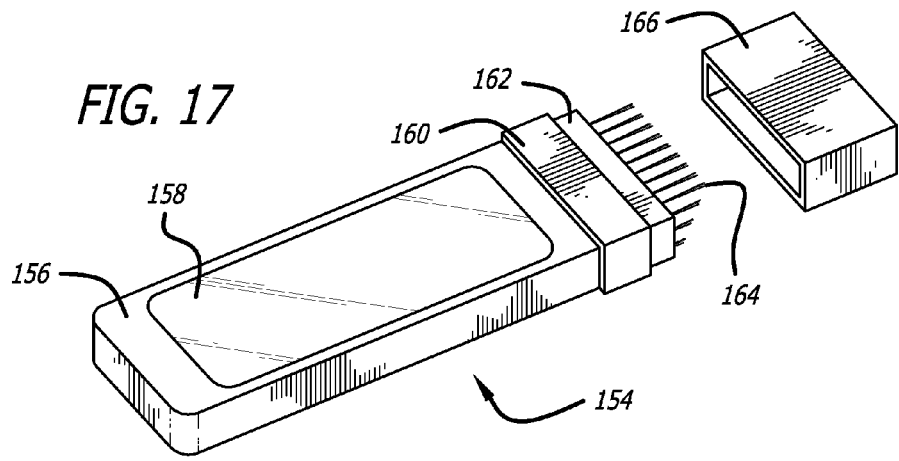
FIG. 17 shows a perspective view of yet another alternative embodiment of the present invention.
Figure 18:
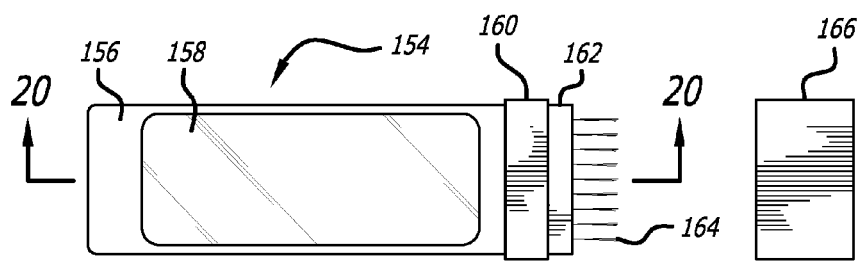
FIG. 18 shows a plan view of the embodiment of FIG. 17.
Figure 19:
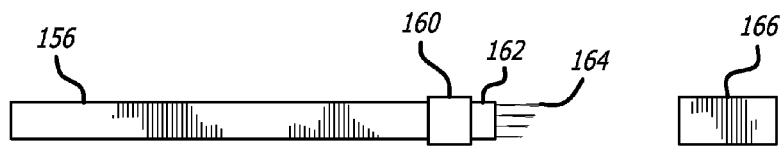
FIG. 19 shows a side view of the embodiment of FIG. 17.

Referring now to FIGS. 17 through 19, yet another alternative embodiment of the device 154 of the present invention is shown. The enclosure 156 is made of a hardened plastic in the preferred embodiment, but may be made of any similar rigid material. In alternative embodiments, the enclosure 156 may be made more flexible.

In this device 154, there is a transparent window 158. The window 158 is made up of a highly-flexible plastic. This window 158 is the place at which a user may apply pressure in order to force the contents of the device 154 out of the device 154. The transparent window 158 also allows a user to see the contents of the device 154 for use in determining when to dispose of the device 154.

This device 160 includes a stop 160 and an edge 162. The edge 162 is immediately adjacent to the tapered bristles 164. The cap 166 fits snugly over the edge 162 and abuts the stop 160 to thereby cover and protect the bristles 164. The cap 166 may also "snap" onto the edge 162 which may include one or more ridges onto which the cap 166 may be designed to fit. This embodiment may also provide for removable bristles which may be removed at the stop and replaced with new bristles to allow for multiple uses.

Figure 20:
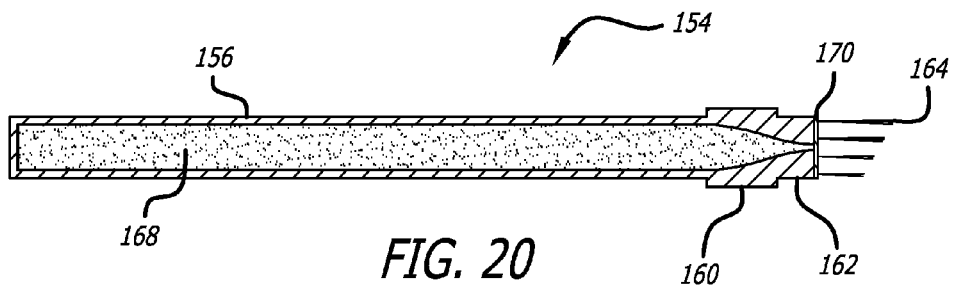
FIG. 20 shows a cross-sectional view of the embodiment of FIG. 17.

Referring now to FIG. 20, a cross-sectional view of the device 154 of FIGS. 17 through 19 is shown. As with previous embodiments, the device 154 enclosure 156 is shown along with the stop 160, the edge 162 and the bristles 164. As in previous embodiments, the bristles 164 are tapered for ease of use and better access to teeth.

Within the device is contained an amount of dentifrice 168. As with prior embodiments, a seal 170 is included to maintain the freshness and hydration of the dentifrice 168. The seal 170 is at the head of the device 154, just beyond the edge 162. The seal 170 may be broken by pressure from the dentifrice 168 as it is squeezed by a user. The seal 170 may also be broken by a sharp point, provided on the cap 166 or otherwise. As with previous embodiments a puncturing point may be provided as a portion of the cap 166 for this purpose.

Figure 21:
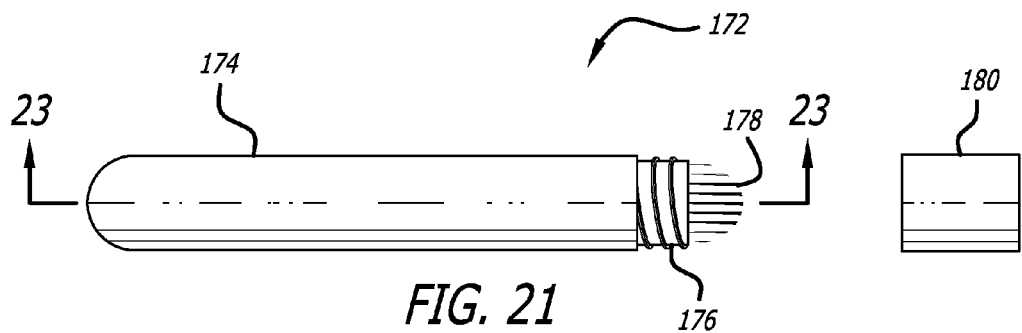
FIG. 21 shows a top view of yet another embodiment of the present invention.
Figure 22:
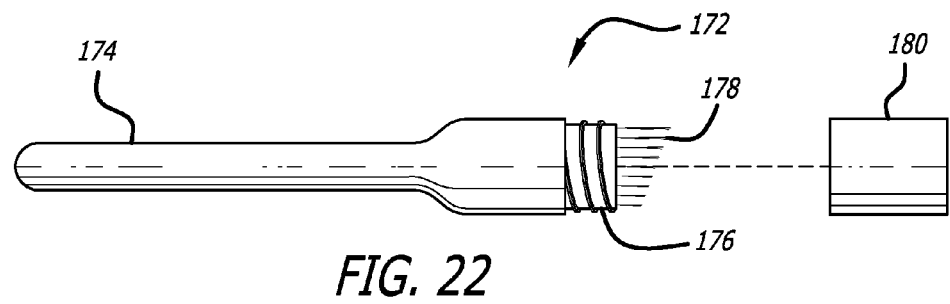
FIG. 22 shows a side view of the embodiment of FIG. 21.
Figure 23:
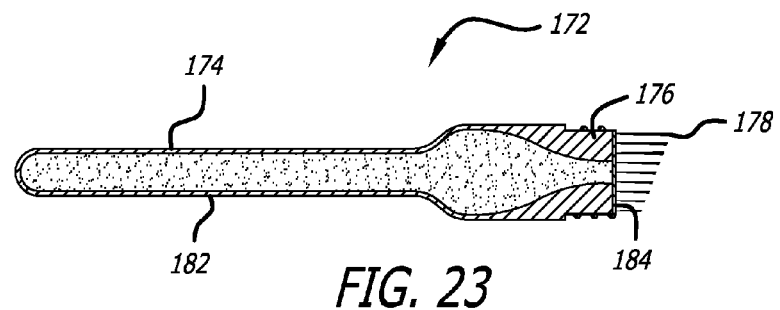
FIG. 23 shows a cross-sectional view of the embodiment of FIG. 21.

Referring now to FIGS. 21 through 23, yet another alternative embodiment of the present invention is shown. The device 172 of this embodiment also has an enclosure 174, preferably made up of a flexible plastic. There are also a threaded neck 176 and tapered bristles 178 to which a cap 180 may be affixed and cover. As with previous embodiments, the cap 180 may include a puncturing point.

A cross-sectional view of the device 172 includes the dentifrice 182 and the seal 184. As with previous embodiments, the seal 184 may break with the pressure applied by dentifrice 182 or may require puncturing prior to the dentifrice leaving the enclosure 174. A puncturing point provided in the cap 180 or otherwise may puncture the seal 184 if necessary.

Figure 24:
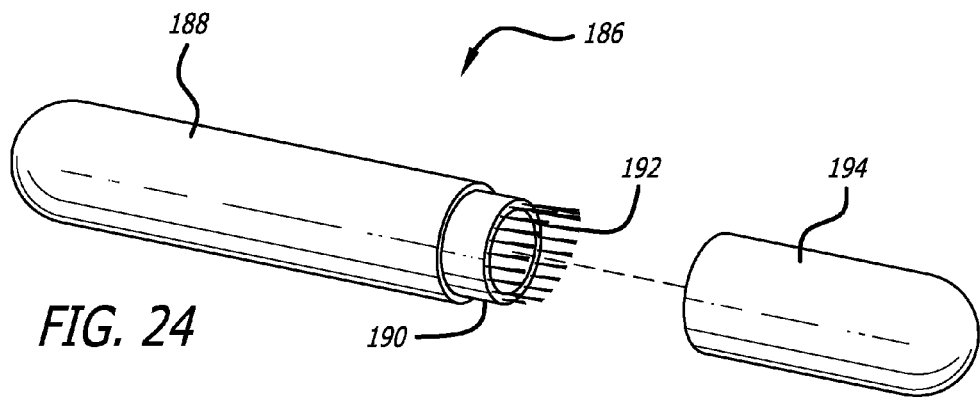
FIG. 24 shows a perspective view of yet another alternative embodiment of the present invention.
Figure 25:
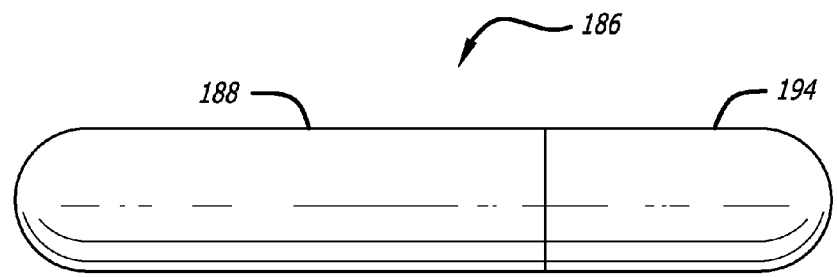
FIG. 25 shows a closed side view of the embodiment of FIG. 24.
Figure 26:
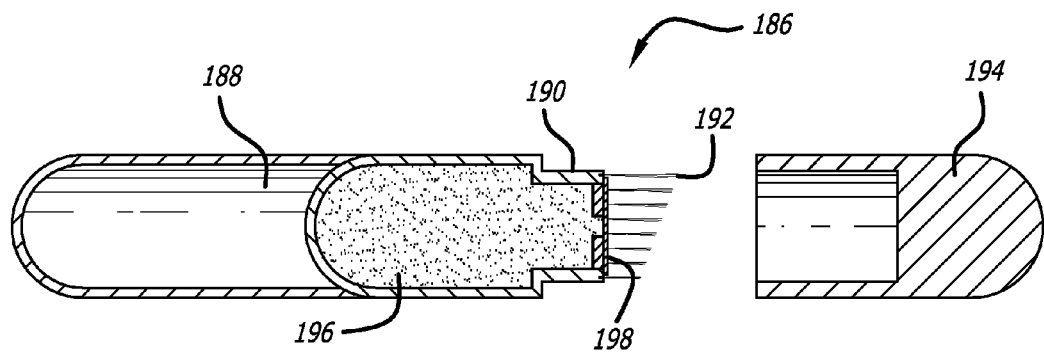
FIG. 26 shows a cross-sectional view of the embodiment of FIG. 24.

Turning now to FIGS. 24 through 26, yet another alternative embodiment of the present invention is shown. In this embodiment, the device 186 includes an enclosure 188, a ridge 190 and tapered bristles 192. Also included is a cap 194 which fits snugly over the ridge 190 to thereby contain and protect the bristles 192. In FIG. 25, the device 186 is shown with the cap 194 attached to the enclosure 188.

In FIG. 26, the device is shown in cross-section. The enclosure 188 is cut-away to show the dentifrice 196 within the enclosure 188. The ridge 190 and the tapered bristles 192 along with the cap 194 are also shown in cross-section.

Also present is the seal 198, as described in previous embodiments. The seal may be broken with an external device. The seal may also open upon the application of pressure upon the enclosure 188. The seal 198 is designed to keep the dentifrice clean, moist and protected while the device is in transit or prior to using.

Figure 27:
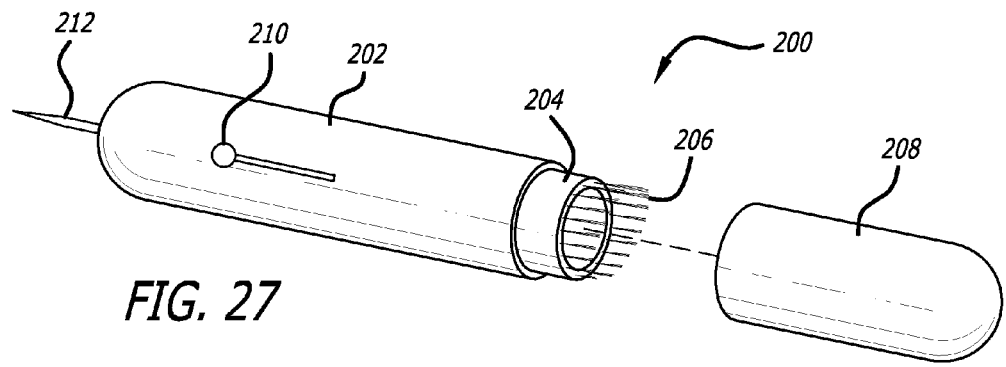
FIG. 27 shows a perspective view of the embodiment of FIG. 24 with an additional element.
Figure 28:
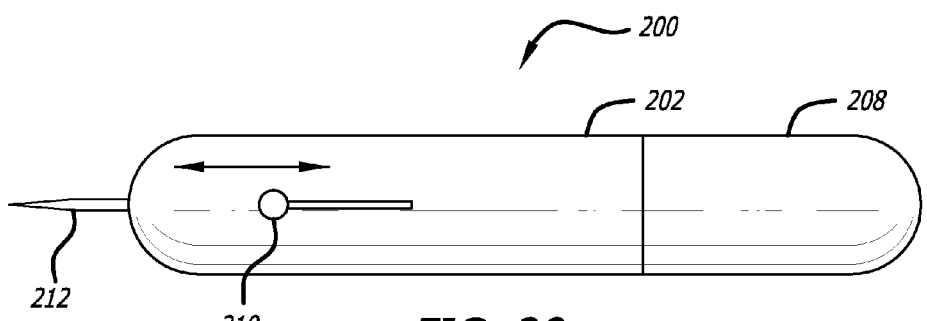
FIG. 28 shows a plan view of the embodiment of FIG. 24 with the additional element.
Figure 29:
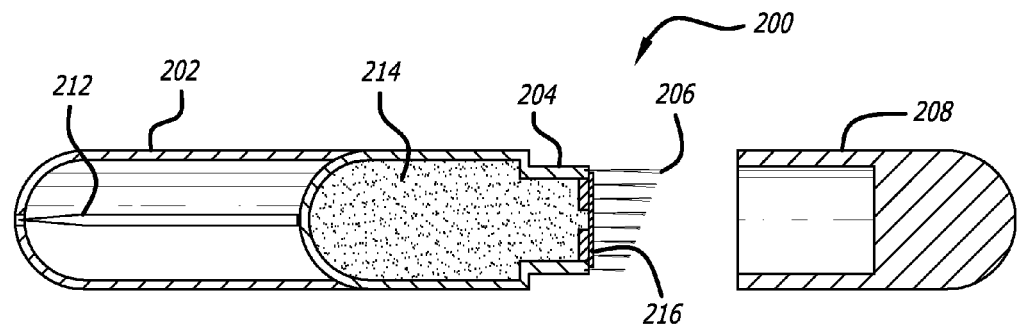
FIG. 29 shows a cross-sectional view of the embodiment of FIG. 24 with the additional element.

Referring now to FIGS. 27 through 29 an embodiment similar to that of FIGS. 23 through 26 is shown. This embodiment includes one additional element that is useful in dental cleaning. The device 200 includes an enclosure 202 a ridge 204, tapered bristles 206 and a cap 208 just as the prior embodiment. However, this embodiment also includes a slider 210 and a built-in toothpick 212.

The slider 210 allows a user to retract and extend the tooth-pick 212. In some embodiments, the slider may be provided with a number of pre-determined internal ridges designed to hold the slider 210 in place such that the toothpick 212 is extended to a particular length. For example, the tooth-pick 212 may be held in place by the slider 210 at positions such as completely extended and completely retracted. The tooth-pick 212 may be provided to a user in this way so that a user may utilize the toothpick to clean larger debris from the user's teeth prior to cleaning the teeth using the bristles 206.

In FIG. 29, the tooth-pick 212 may be seen in the completely-retracted position within the enclosure 202. The dentifrice 214 may also be seen along with the seal 216 as shown in other embodiments. The seal 216 may be broken by external devices or by the pressure applied to the enclosure 202 by a user.

Figure 30:
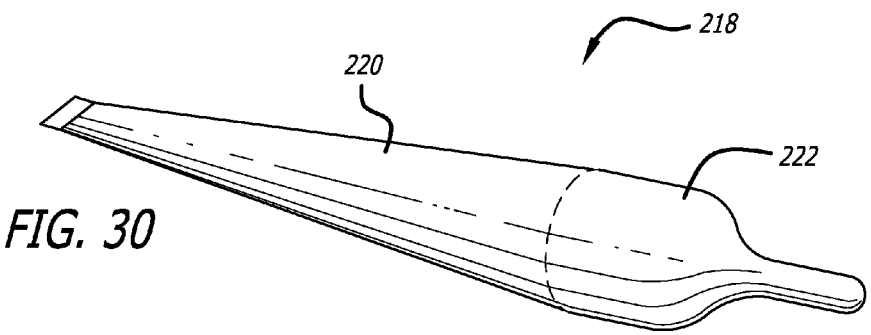
FIG. 30 shows a perspective view of another alternative embodiment of the present invention.
Figure 31:
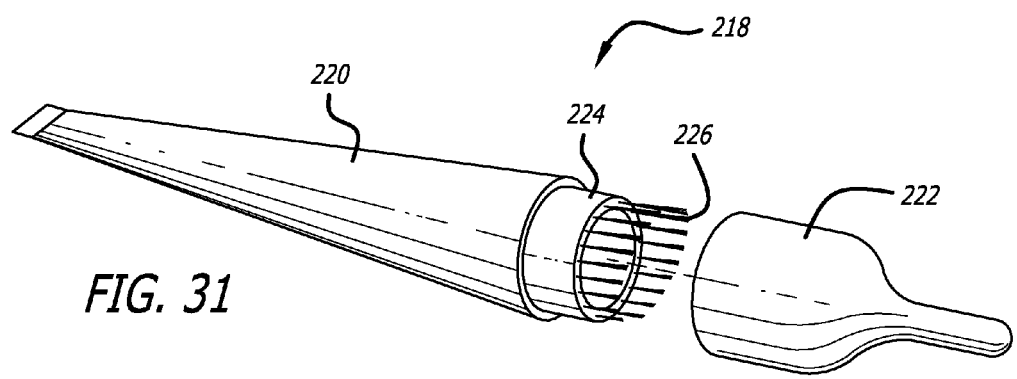
FIG. 31 shows a perspective view of the embodiment of FIG. 30 with the cap removed.
Figure 32:
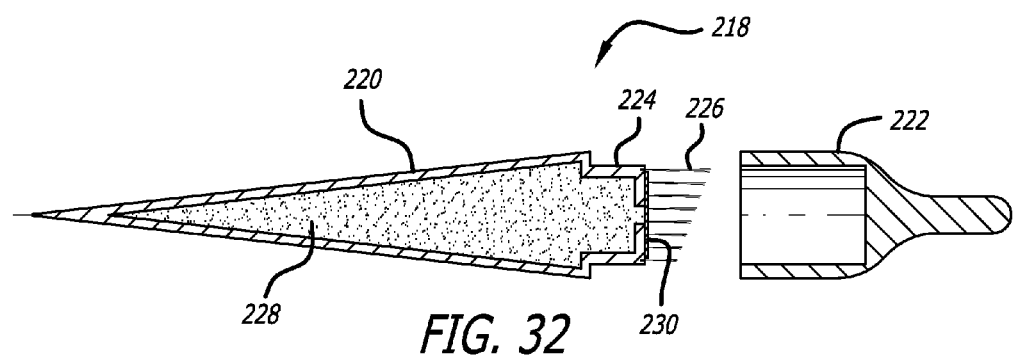
FIG. 32 shows a cross-sectional view of the embodiment of FIG. 30.

Turning now to FIGS. 30 through 32, yet another alternative embodiment of the present invention is shown. In FIG. 30, the device 218 of the present invention is shown in a closed position. The cap 222 is affixed to the enclosure 220. In FIG. 31, it can be seen that the enclosure 220 includes a ridge 224 and tapered bristles 226 as in previous embodiments. The cap 222 has been removed to allow for this view.

This embodiment is generally made of a thin plastic or alloy. The tapered end of the enclosure 220 allows for easier manufacture by machines. The end is simply "crimped" in order to close off each container during manufacture.

In FIG. 32, a cross-sectional view of this embodiment is shown. The enclosure 220, ridge 224 and tapered bristles 226 may be seen along with the cap 222. As with previous embodiments the dentifrice 228 is protected by a seal 230. The seal serves to keep the dentifrice 228 moist and protected during transit and before use.

Figure 33:
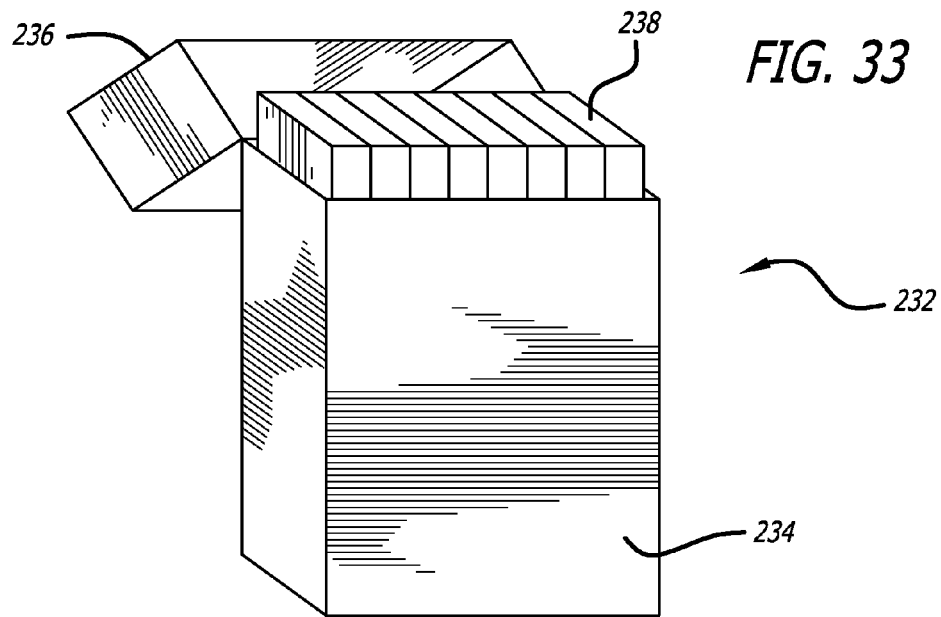
FIG. 33 shows one embodiment of the packaging of the present invention.

Turning now to FIGS. 33 through 36, various containers for the safe transport, containment and sale of any of the embodiments disclosed are shown. In FIG. 33, a cigarette-carton-like container 232 is shown. The container 232 includes a rectangular base 234 and a rectangular top 236. The top of the container 232 may sit snugly over the devices 238 enclosed within. The container 232 fully encloses the devices 238 within so that they may be protected from elements which may contaminate them.

Figure 34:
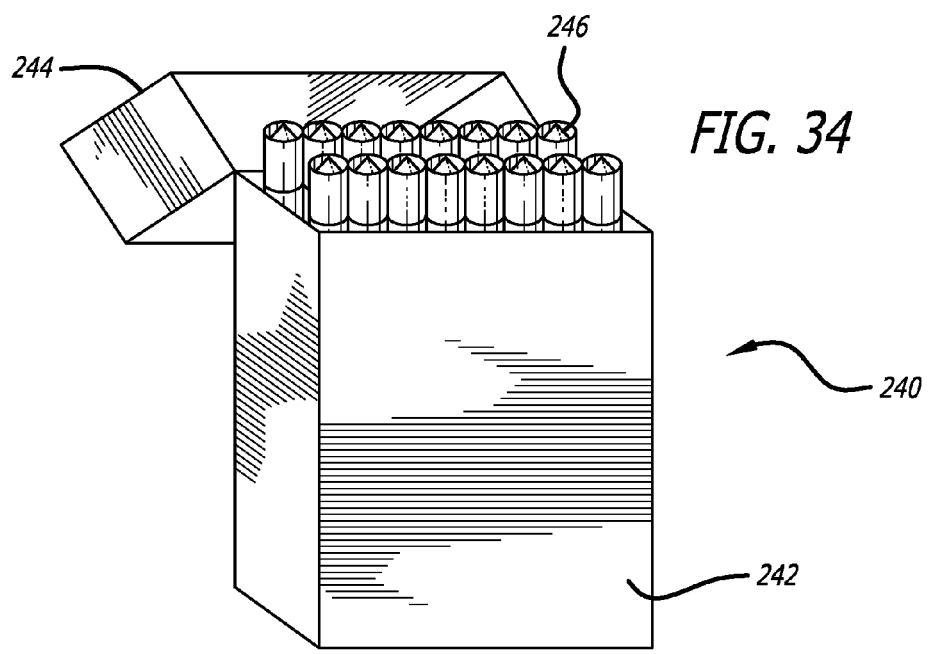
FIG. 34 shows an alternative embodiment of the packaging of the present invention.

Turning now to FIG. 34, a similar container 240 is shown, also include a rectangular open base 242 and a flip top 244. The base 242 is designed in such a way that it my accept a multiplicity of dental cleaning devices. FIG. 33 demonstrates that various types of devices 246 may be enclosed within this type of container 240. Multiple rows of devices 246 may be enclosed within the container 240, dependent upon their size and marketing desires of the manufacturer or retailer.

Figure 35:
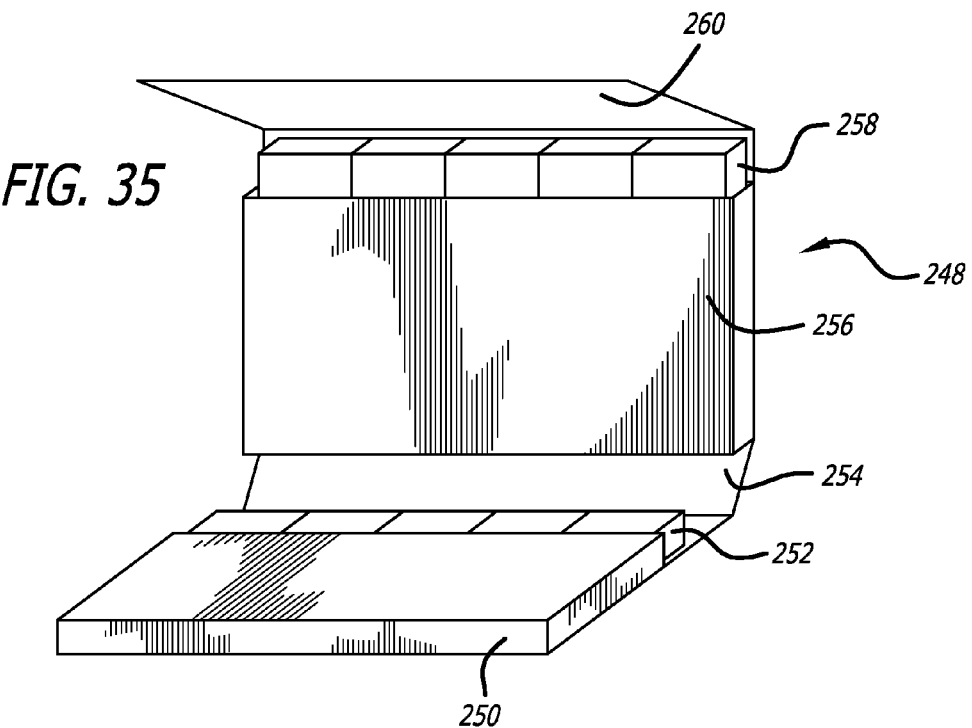
FIG. 35 shows yet another embodiment of the packaging of the present invention.

Referring now to FIG. 35, another alternative container 248 is shown. This container is split into two portions a base portion 250, containing a plurality of devices 252 and an upper portion 256, connected by a cardboard or plastic backing 254, also containing a plurality of devices 258. The backing 254 allows the device 248 to be folded in half wherein the upper portion 256, made up of three side walls and a front, and the base portion 250, also made up of three side walls and a front, may abut one another and an upper flap 260 may then cover both portions to securely hold the device 248 in a closed position.

Figure 36:
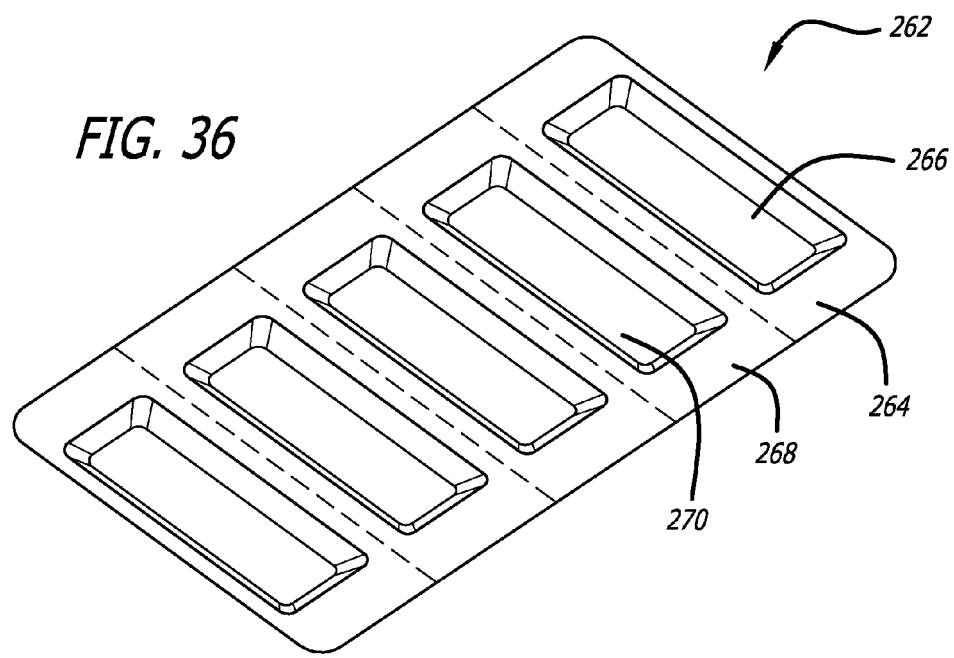
FIG. 36 shows yet another embodiment of the packaging of the present invention.
Figure 37:
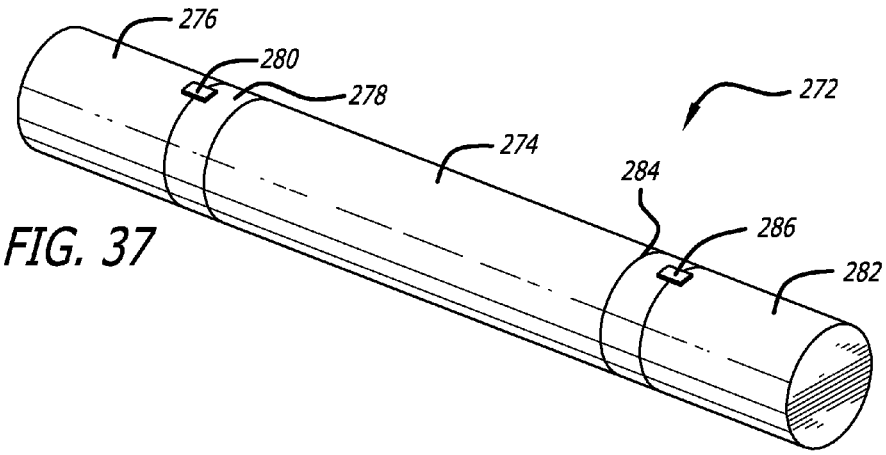
FIG. 37 shows a perspective view of alternative dental cleaning apparatus.

Yet another alternative embodiment for a container 262 is shown in FIG. 36. In this embodiment, the container 262 defines a break-away blister pack which is made up of a series of plastic (in the preferred embodiment) portions perforated such that they may be split into individual containers. Each perforated portion 264 contains an indentation 266 suitable for the placement of one dental cleaning device. Other perforated portions, such as second perforated portion 268, also include indentations, such as indentation 270, for use in storing additional dental cleaning devices.

The container 262 may be enclosed with a cardboard top (not shown) which may also be perforated. Accordingly, a user may "tear off" one or more dental cleaning device, such as one enclosed within the perforated portion 264 for later use. These portions 264 may then be opened and the dental cleaning device removed, used and, if a user so desires, disposed.

Referring now to FIGS. 37 through 44, a different device 272 for dental cleaning and the method of it's use is shown. In the preferred embodiment of this invention, the entire device is made of hardened plastic. This device 272 is made up of a number of compartments. There is a brush compartment 274 connected to a dentifrice compartment 276. The dentifrice compartment 276 includes a cap 278 attached to the dentifrice compartment 276 by a hinge 280.

Figure 38:
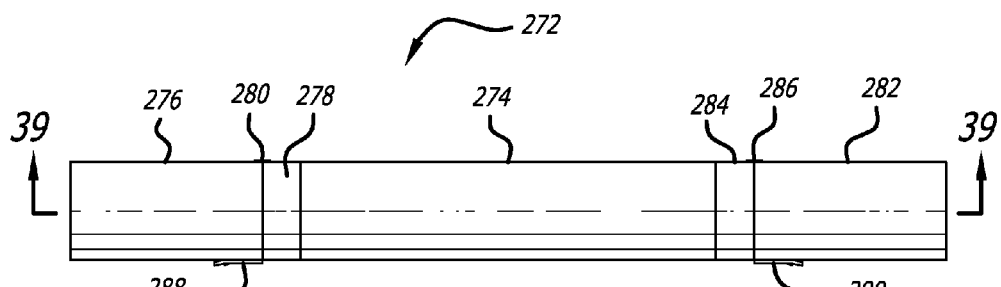
FIG. 38 shows a plan view of the alternative dental cleaning apparatus of FIG. 37.

A third compartment 282 is connected to the brush compartment 274 by way of a cap 284 also connected by a hinge 286. The interaction of hinges 280 and 286 in conjunction with the caps 278 and 284 is seen more clearly in FIG. 43. Also visible in FIG. 38 are the two snap-tight closures 288 and 290 that are used to secure the dentifrice compartment 276 and cleansing fluid compartment 282 to their respective caps 278 and 284. It is to be understood that this embodiment may be square or rectangular in cross-section as well as the round cross-section that is depicted.

Figure 39:
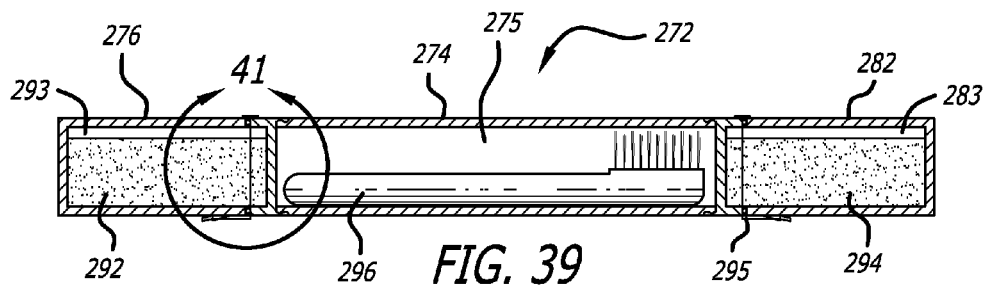
FIG. 39 shows a cross-sectional view of the alternative dental cleaning apparatus of FIG. 37.
Figure 40:
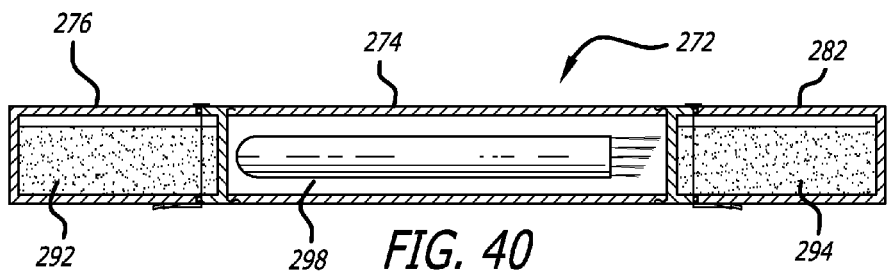
FIG. 40 shows an alternative cross-sectional view of the alternative dental cleaning apparatus of FIG. 37.

Referring now to FIGS. 39 and 40, cross-sectional views of the device 272 can be seen. In these views the brush compartment 274, including inner chamber 275, the dentifrice compartment 276 and the cleansing fluid compartment 282 may all be seen. In this embodiment the dentifrice compartment 276 includes a hollow chamber 291 which is filed with dentifrice 292. The cleansing fluid compartment 282, including a second hollow chamber 283 is filled with cleansing fluid 294.

The dentifrice 292 may be applied to the brush 296 for use in cleaning the teeth. The cleansing fluid 294 may then be used in the absence of or in conjunction with an external water source, to wash and rinse the brush 296. In FIG. 40, an alternative brush 298 is shown. It is to be understood that a variety of brush types may be used.

Referring now to FIG. 41, a close-up of a portion of FIG. 39 is shown. In this Figure the brush compartment 274 includes an inner chamber 275 (see FIG. 39), the dentifrice compartment 276 and the cap 278 may be seen in cross-section. The hinge 280 and snap-tight closure 288 may also be seen. The snap-tight closure 288 acts in such a way that a small protuberance 310 (see FIG. 43) from the exterior of the dentifrice compartment 276 holds the closure 288 in place once it has been pressed over the protuberance.

In this cross-section, seals 300 which encircle the entire circumference of the dentifrice compartment 276 where it meets the cap 278 are also shown. These seals 300 serve to ensure that the second compartment 276 does not leak out its dentifrice 292. Similar seals, such as seal 295 (see FIG. 39), are provided in the cleansing fluid compartment to contain the cleansing fluid 294. These seals serve to keep the brush, dentifrice and dental cleaning fluid (in some embodiments) separated from the atmosphere.

FIG. 41 also shows the snap-in two-part attachment mechanism for the cap 278 to the brush compartment 274. A ridge 302 extends from one end of the cap 278. The ridge 302 is circular when viewed from above. This ridge 302 fits snugly into a corresponding groove 304 in the brush compartment 274. This allows the brush compartment 274 to be combined with the dentifrice compartment 274 for transport and storage.

The removal of the brush 298 from the brush compartment 274 may be seen in FIG. 42. The brush compartment 274 is also being removed from the cleansing fluid compartment 282, containing cleansing fluid 294. The tooth 308 and corresponding groove 306 allow the two compartments to be transported together while also allowing for separation for use.

Referring now to FIG. 43, the separated dentifrice compartment 276 is shown. In this Figure, the dentifrice 292 is shown, along with the hinge 280, now in a bent position for opening. The ridge 302 is shown extending upwards from the cap 278. Simultaneously, the snap-tight closure 288 is shown, along with the protuberance 310 to which it affixes when the cap 278 is closed.

A perspective view of the separated dentifrice compartment 276 along with the brush 298 is shown in FIG. 44. In this Figure, the cap 278 attached to the dentifrice compartment 276 can be seen. A more clear depiction of the snap-tight closure 288 and the corresponding protuberance 310 may also be seen. Similarly, the seal 300, extending around the entire circumference of the dentifrice compartment 276 top can be seen. The brush 298 is shown in the midst of applying dentifrice to its bristles for application and use on a user's teeth. In this embodiment, the separate compartments may also be attachable to one another by way of a threaded neck and corresponding threaded compartment as seen in previous figures.

Figure 45:
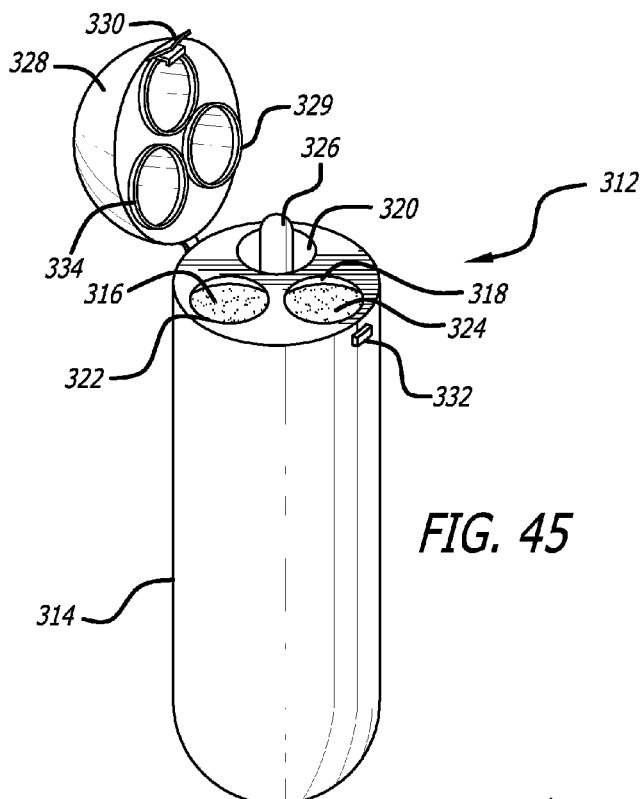
FIG. 45 shows an alternative dental cleaning apparatus.
Figure 46:
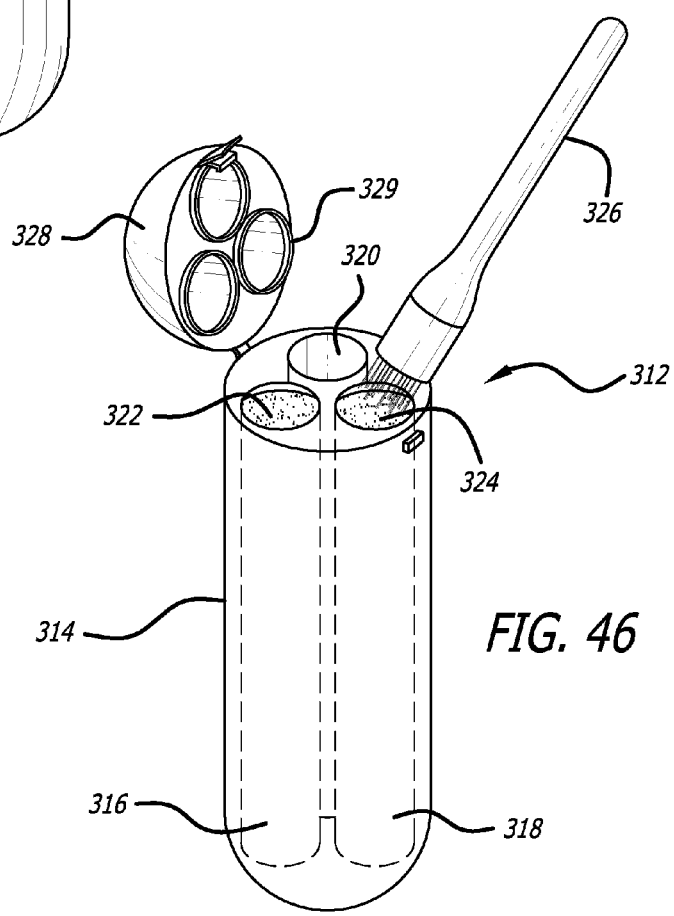
FIG. 46 shows the alternative dental cleaning apparatus of FIG. 45 in use.

Referring now to FIGS. 45 and 46, an alternative embodiment of a dental cleaning device 312 is shown. The base 314 of the device 312 includes three compartments 316, 318 and 320. The first compartment 316 is filed with dentifrice 322. The second compartment 318 is filed with cleansing fluid 324. The third compartment 320 includes a brush 326.

The cap 328 includes corresponding compartments with seals, such as seal 334 for ensuring that none liquid may exit the device 312 once it is closed. The cap 328 includes a snap-tight closure, which corresponds to a protuberance 332. When closed the device 312 is designed including the seals such that it is substantially air-tight. As above, it is to be expressly understood that this embodiment may take on any number of cross-sectional shapes including squares or rectangles.

Referring now to FIG. 46 specifically, the device 312 is shown such that the depth of the chambers 316, 318 and 320 may be seen within the base 314. The cap 328 is opened and the brush 326 is removed such that cleansing fluid 324 may be applied to clean the brush 326, for example, after brushing the teeth. When closed, the cap 329 includes seals, such as seal 329, which maintain each compartment separate from the atmosphere.

Figure 47:
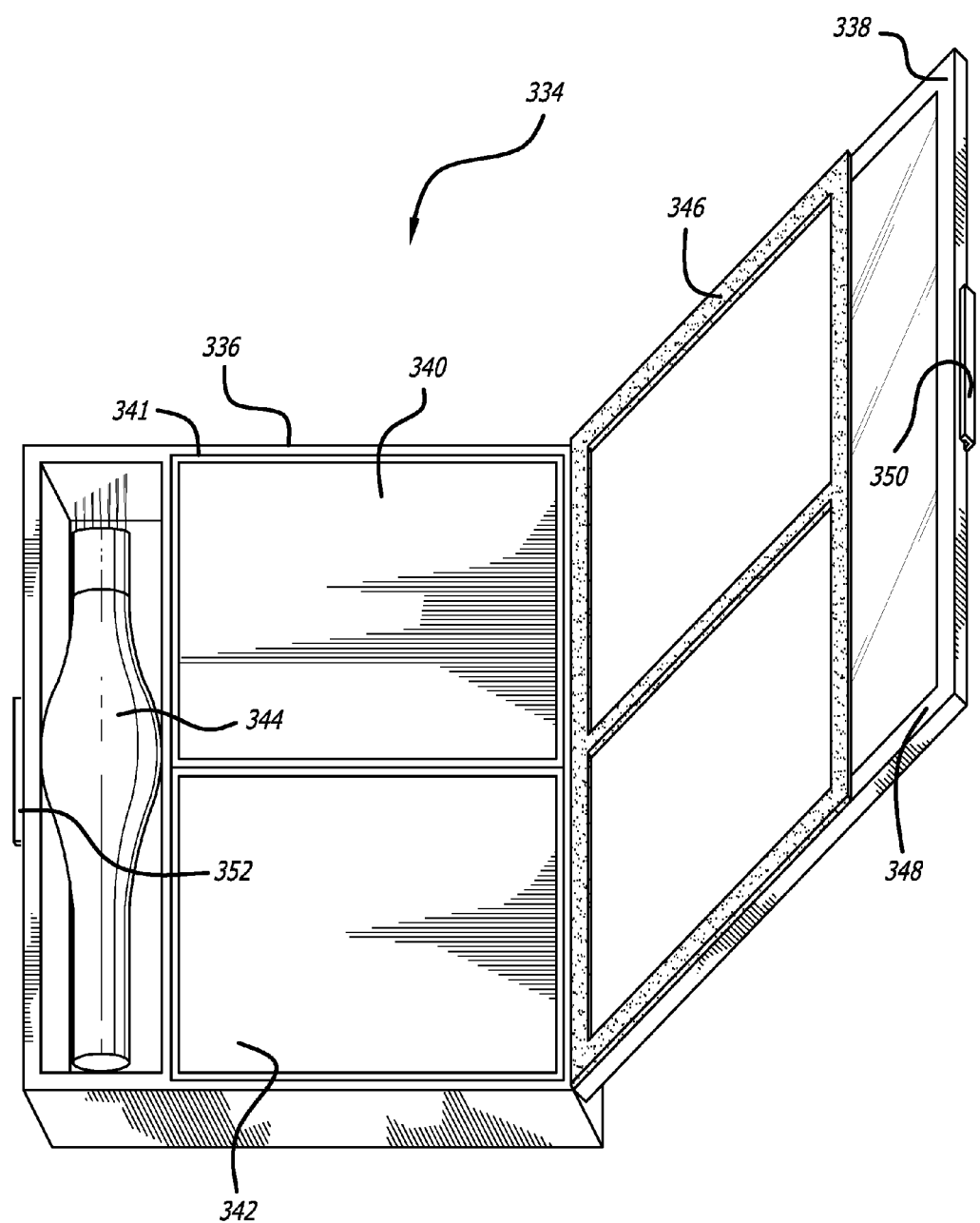
FIG. 47 shows yet another alternative dental cleaning apparatus.

An alternative embodiment is shown in FIG. 47. This device 334 includes a base 336 and a lid 338. The device 334 contains a dentifrice compartment 340 a cleansing fluid compartment 342 and a brush 344, also contained with a compartment. In some embodiments, the dentifrice compartment 340 and the cleansing fluid compartment 342 may be removable. In these cases, removable portions, such as portion 341 may be removed when the dentifrice has been depleted and may be replaced with a new portion 341 including a new dentifrice compartment 340. Both the dentifrice compartment 340 and cleansing fluid compartment 342 are provided with a seal 346 in the lid 338 of the device 334. The seal 346 ensures that dentifrice or cleansing fluid do not escape the device 334 into a user's purse, for example, while in transit.

In this embodiment, the compartments 340 and 342 containing a dentifrice and cleansing fluid respectively, may, as an alternative, be removable and replaceable in order for the option of a variety of dentifrice flavors, and the option of omitting the cleaning fluid. Furthermore, in this alternative embodiment, the brushes are also replaceable. As a result, this embodiment could be less expensive to replace individual components. Also, this embodiment could be manufactured including a higher-quality, stylish exterior portion not intended to be replaced.

The device 334 may also include a mirror 348 for viewing one's teeth while using the brush 344. The device 334 is closed such that the lid 338 and the base 336 abut one another. In this position the seal 346 covers the dentifrice compartment 340 and the cleansing fluid compartment 342 and keeps the brush 344 relatively contained. The clasp 350 on the lid 338 snaps closed over a wide protrusion 352 on the base 336.

Figure 48:
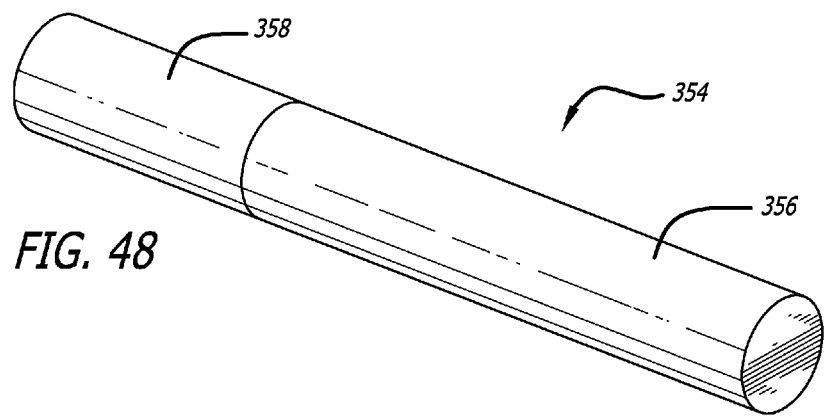
FIG. 48 shows a perspective view of yet another dental cleaning apparatus.
Figure 49:
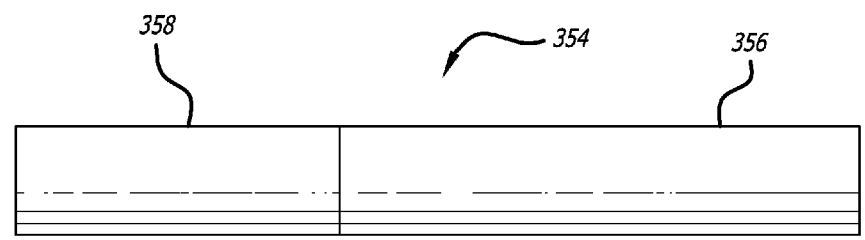
FIG. 49 shows a plan view of the dental cleaning apparatus of FIG. 48.
Figure 50:
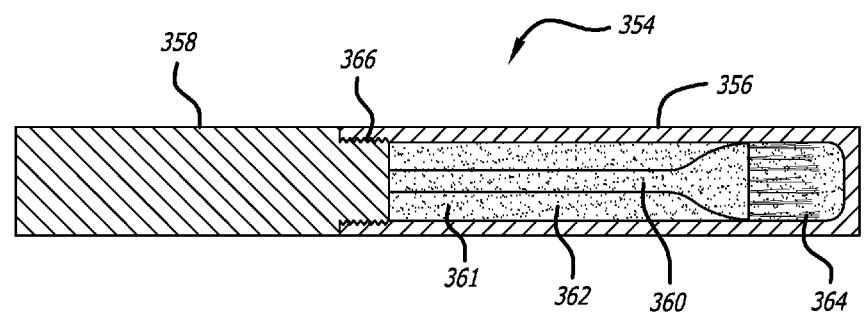
FIG. 50 shows a cross-sectional view of the dental cleaning apparatus of FIG. 48

Referring now to FIGS. 48 through 50, another alternative embodiment of the present invention is shown. In this embodiment, the device 354 includes a lower portion 356 and an upper portion 358. The device 354 may be seen in a perspective view and a side view in FIGS. 48 and 49.

In FIG. 50, a cross-sectional view of the device 354 is shown. In this view it can be seen that the upper portion 358 is solid, while the lower portion 356 is substantially hollow including a hollow cavity 361. The lower portion 356 houses a brush 360, attached to the upper portion 358, that in the closed position is completely submerged in dentifrice 362 such that the bristles 364 of the brush 360 are completely covered in dentifrice for use in cleaning teeth.

The upper portion 358 is affixed to the lower portion 356 by means of threads 366. In alternative embodiments, threads may not be used and instead a tooth and groove or a "snap-in" connection may be used. In any such embodiments, the device 354 be substantially air-tight to protect the dentifrice 362 and to ensure that the device 354 does not leak when closed.

Figure 51:
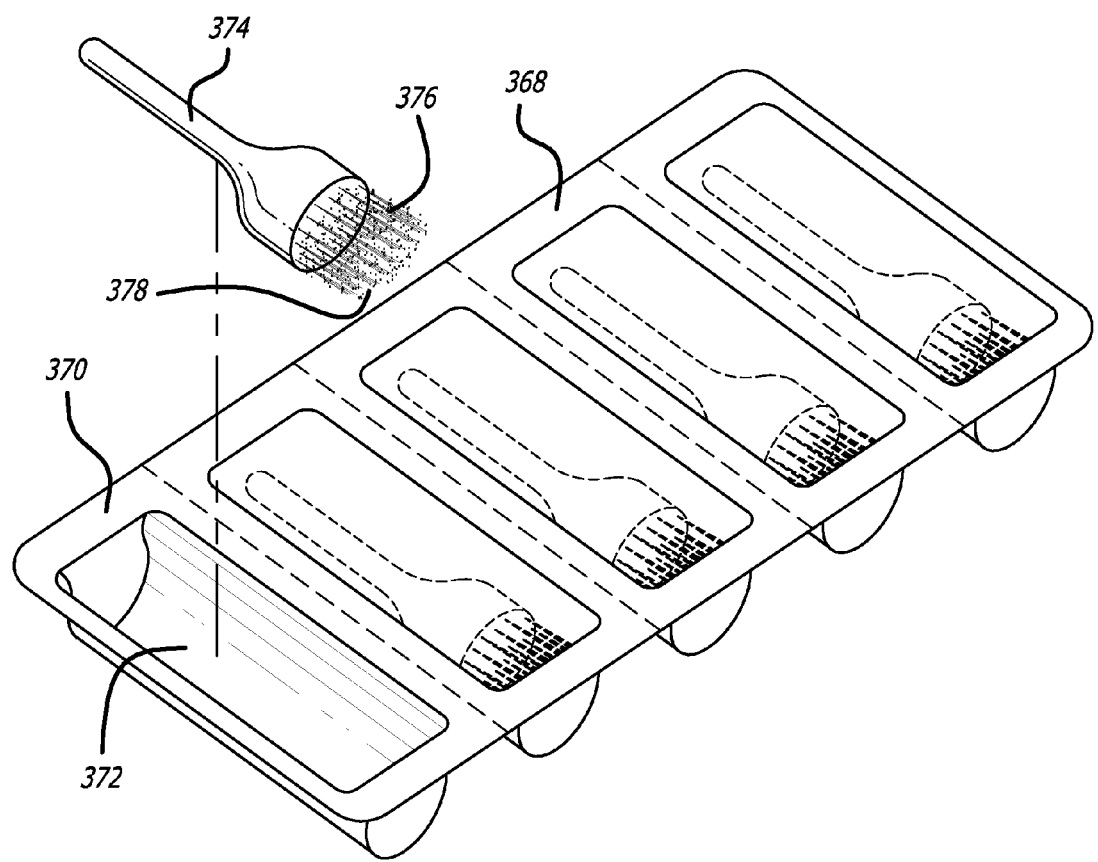
FIG. 51 shows an alternative dental cleaning apparatus.

An additional embodiment is shown in FIG. 51. In the device 368 of this embodiment, a plastic backing 370 is provided with a series of indentations (As shown in FIG. 36), such as indentation 372. Into these indentations, a brush 374 may be placed. In this embodiment the bristles 376 of this brush have been pre-treated with sufficient amounts of dentifrice 378 to allow a user to remove the brush 374 from the device 368 and begin brushing immediately.

A user may "snap off" or "push out" one or more brushes, each contained within an indentation, such as indentation 372, and covered with a cardboard or other backing. The backing is applied such that the brush is maintained in a substantially air-tight state. The pre-treated brush 374 may also be individually wrapped in any number of packages. This way the dentifrice 378 does not harden or otherwise become unsuitable for use. The user may then open the single indentation 372 and remove the brush 374 for use. Once the user has cleaned his or her teeth, the brush 374 may be disposed.

Accordingly, a dental cleanser and stain prevention apparatus has been described. It is to be understood that the foregoing description has been made with respect to specific embodiments thereof for illustrative purposes only. The overall spirit and scope of the present invention is limited only by the following claims, as defined in the foregoing description.

The invention claimed is:

1. A dental cleaning device comprising:
    a pliable chamber enclosing an area sufficient for a small portion of dental cleanser; dental cleanser enclosed within said pliable chamber;
    a tubular neck, affixed to one end of said pliable chamber, through which said dental cleanser may pass;
    a set of bristles, extending from the exterior end of said tubular neck, for use in applying the dental cleanser;
    a seal, disposed within said tubular neck, for preventing said dental cleanser from having contact with the exterior atmosphere prior to use of the dental cleaning device, said seal being breakable to enable release of at least a portion of said dental cleanser;
    and, a cap, removably affixed to said tubular neck, for housing said set of bristles and for preventing said seal from breaking and releasing said dental cleanser when said cap is in place wherein said cap includes a puncturing point thereon for puncturing said seal.

2. The dental cleaning device of claim 1, wherein said dental cleanser is a tooth paste.

3. The dental cleaning device of claim 1, wherein said pliable chamber includes at least one translucent portion through which said dental cleanser is visible.

4. The dental cleaning device of claim 1, wherein said bristles are configured to be tapered for ease of use.

5. The dental cleaning device of claim 1, comprising:
    a retractable toothpick enclosed within said pliable chamber; and
    a means for extending and retracting said toothpick.

6. The dental cleaning device of claim 1, wherein the device is housed within disposable packaging including an open base connected to a flip top, suitable for single-device dispensation.

7. The dental cleaning device of claim 1, housed within disposable packaging comprising:
    a first segment, including a first backing, three surrounding walls, and a first front, wherein said first front covers only a portion of a first device;
    a second segment, including a second backing, connected to said first backing, three surrounding walls and a second front, wherein said second front abuts with said first front when said disposable packaging is closed; and
    a cover flap, adapted to abut the back of said first backing when said disposable packaging is closed.

8. The dental cleaning device of claim 1, housed within a break away blister pack.

9. The dental cleaning device of claim 1, housed within a single plastic wrapper.

10. The dental cleaning device of claim 1, wherein said tubular neck is threaded.

11. The dental cleaning device of claim 1, wherein said dental cleanser is a dentifrice.

* * * * *